United States Patent
Cho et al.

(10) Patent No.: US 8,232,083 B2
(45) Date of Patent: Jul. 31, 2012

(54) **METHOD OF PRODUCING LYCOPENE USING RECOMBINANT *ESCHERICHIA COLI***

(75) Inventors: Nahm Ryune Cho, Daejeon (KR); Min Soo Park, Daejeon (KR); Dong Hyun Lee, Daejeon (KR); Ho Seung Chung, Seoul (KR); Jong Keun Kim, Daejeon (KR)

(73) Assignee: Amicogen Co., Ltd., Gyungsangnam-Do (KR)

( * ) Notice: Subject to any disclaimer, the term of this patent is extended or adjusted under 35 U.S.C. 154(b) by 247 days.

(21) Appl. No.: 12/598,808

(22) PCT Filed: May 6, 2008

(86) PCT No.: PCT/KR2008/002535
§ 371 (c)(1),
(2), (4) Date: Apr. 6, 2010

(87) PCT Pub. No.: WO2008/136632
PCT Pub. Date: Nov. 13, 2008

(65) Prior Publication Data
US 2010/0227370 A1    Sep. 9, 2010

(30) Foreign Application Priority Data
May 4, 2007  (KR) ........................ 10-2007-0043682

(51) Int. Cl.
*C12P 5/02* (2006.01)
*C12P 23/00* (2006.01)
*C12P 7/00* (2006.01)
*C12P 21/06* (2006.01)
*C12P 19/34* (2006.01)
*C12N 1/20* (2006.01)
*C12N 15/74* (2006.01)
*C12N 15/00* (2006.01)
*C07H 21/04* (2006.01)

(52) U.S. Cl. ..... 435/167; 435/67; 435/132; 435/252.33; 435/252.3; 435/471; 435/69.1; 435/91.1; 435/320.1; 536/23.1; 536/23.2

(58) Field of Classification Search ................ 435/167, 435/67, 132, 252.33, 252.3, 471, 69.1, 91.1, 435/320.1; 536/23.1, 23.2
See application file for complete search history.

(56) References Cited

U.S. PATENT DOCUMENTS

| | | | |
|---|---|---|---|
| 5,429,939 A | 7/1995 | Misawa et al. | |
| 5,530,189 A | 6/1996 | Ausich et al. | |
| 6,087,152 A | 7/2000 | Hohmann et al. | |
| 6,696,282 B2 | 2/2004 | Jones et al. | |
| 6,706,516 B1 | 3/2004 | Liao | |
| 7,063,956 B2 | 6/2006 | Pasamontes et al. | |

FOREIGN PATENT DOCUMENTS
KR        1020070082647 A        8/2007

OTHER PUBLICATIONS

Abstract of Korean Patent No. KR1020040085369 dated Oct. 8, 2004, 1 page.
Kucuk, et al., "Phase II Randomized Clinical Trial of Lycopene Supplementation before Radical Prostatectomy", *Cancer Epidemiology*, 10, 861-868, 2001.
Misawa, et al., "Metabolic engineering for the production of carotenoids in non-carotenogenic bacteria and yeasts", *J. of Biotechnology*, 59, 169-181, 1998.
Neuman, et al., "Reduction of exercise-induced asthma oxidative stress by lycopene, a natural antioxidant", *Allergy*, 55, 184-1189, 2000.
Rissanen, et al., "Lycopene, Atherosclerosis, and Coronary Heart Disease", *Exp Blot Med(Maywood)*, 227, 900-907, 2002.
Zhou, et al.,"DNA Recovery from Soils of Diverse Composition", *Applied and Environmental Microbiology*, 62, 2, p. 316-322, 1996.
Search Report and Written Opinion for PCT/KR2008/002535 dated Aug. 21, 2008, 10 pages.

*Primary Examiner* — Ganapathirama Raghu
(74) *Attorney, Agent, or Firm* — Dority & Manning, P.A.

(57) ABSTRACT

A method of producing lycopene with high productivity by means of a recombinant bacterial strain includes preparing the recombinant vector containing genes encoding proteins, which are required for lycopene biosynthesis. The genes involved in lycopene biosynthesis are crtE, crtB and crtI, and at least one of the said three genes (crtE, crtB and crtI) is selected from the group consisting of crtE with the nucleotide Sequence 1, crtB with the nucleotide Sequence 3 and crtI with the nucleotide Sequence 5, of the Sequence List. The said recombinant vector is transformed into *Escherichia coli*.

5 Claims, 8 Drawing Sheets

[Fig. 1]
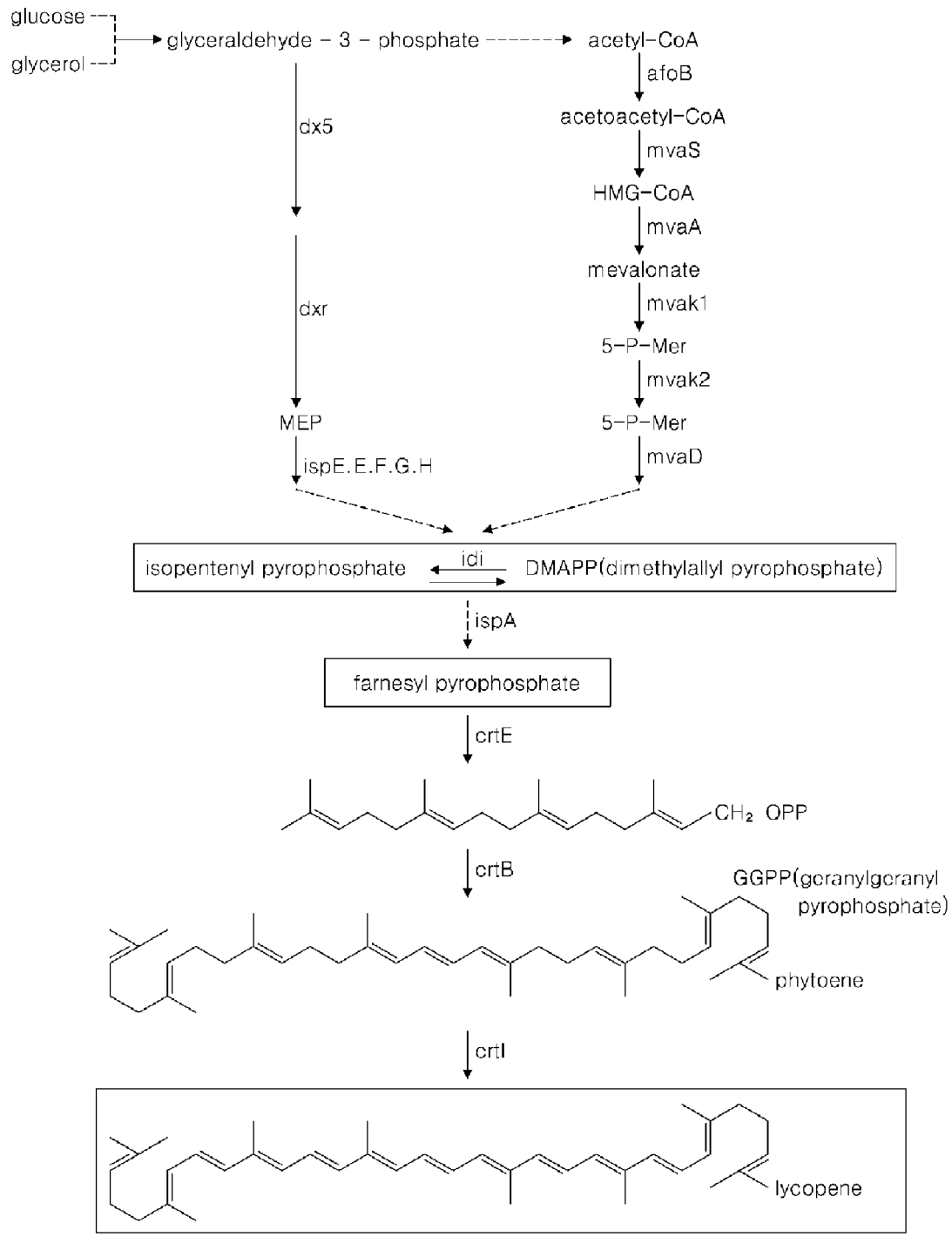

[Fig. 2]
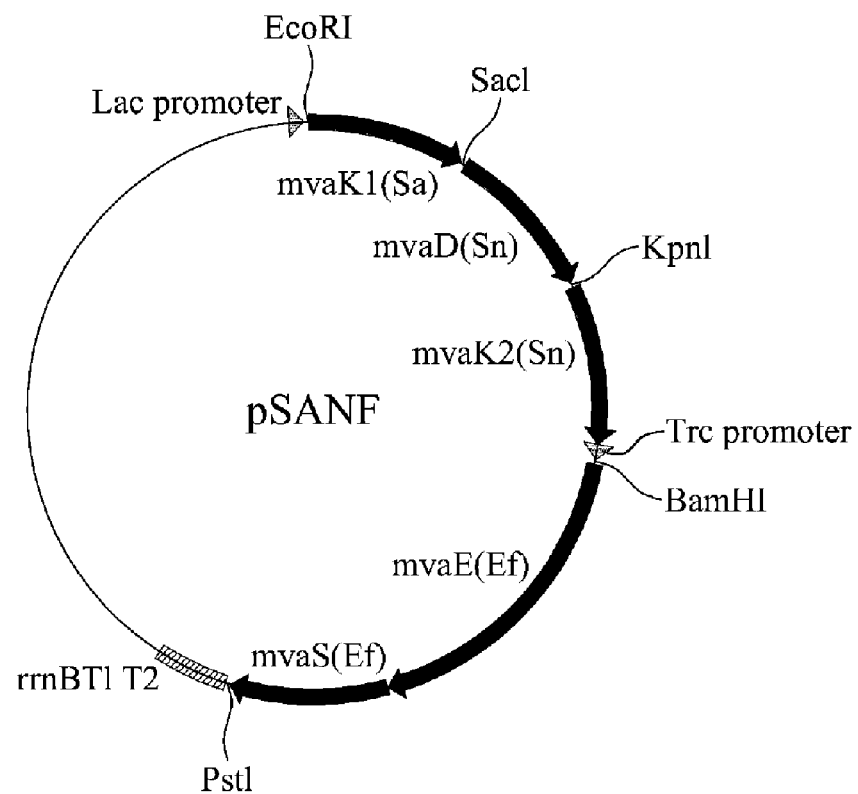

[Fig. 3]
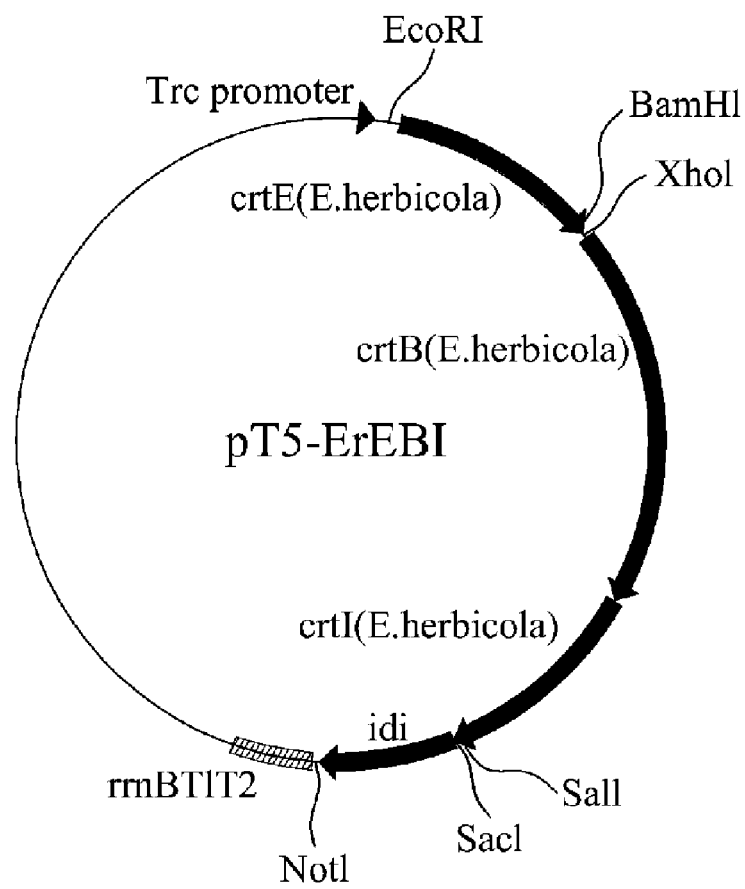

[Fig. 4]
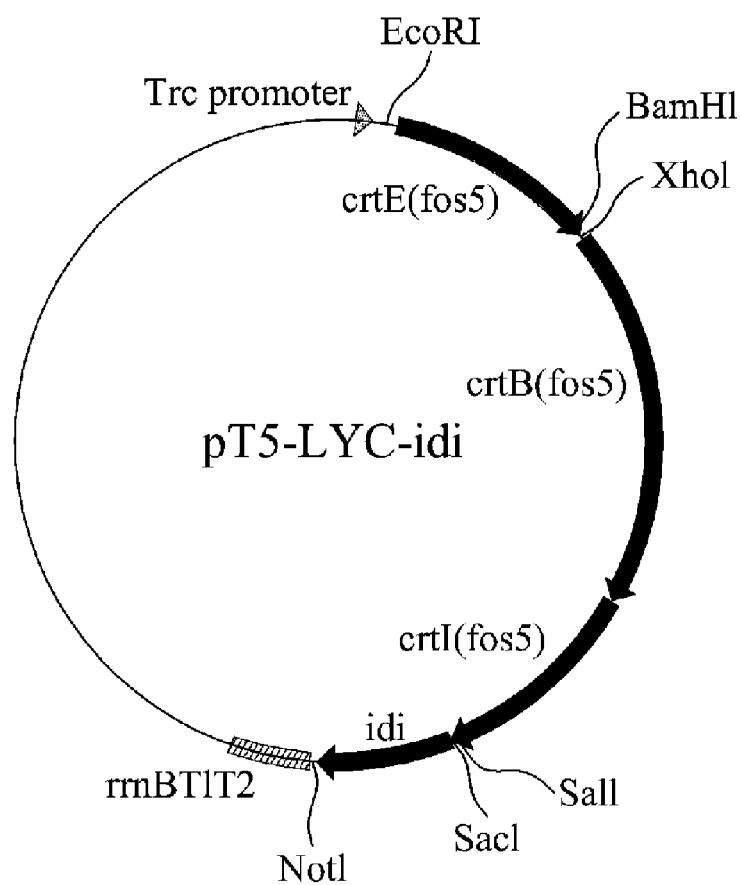

[Fig. 5]
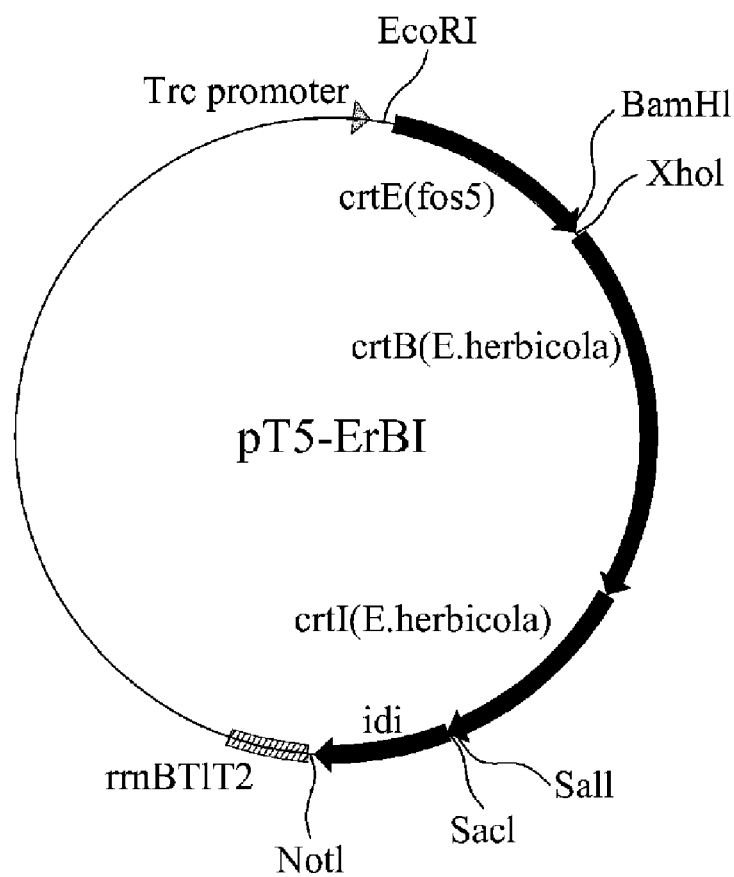

[Fig. 6]
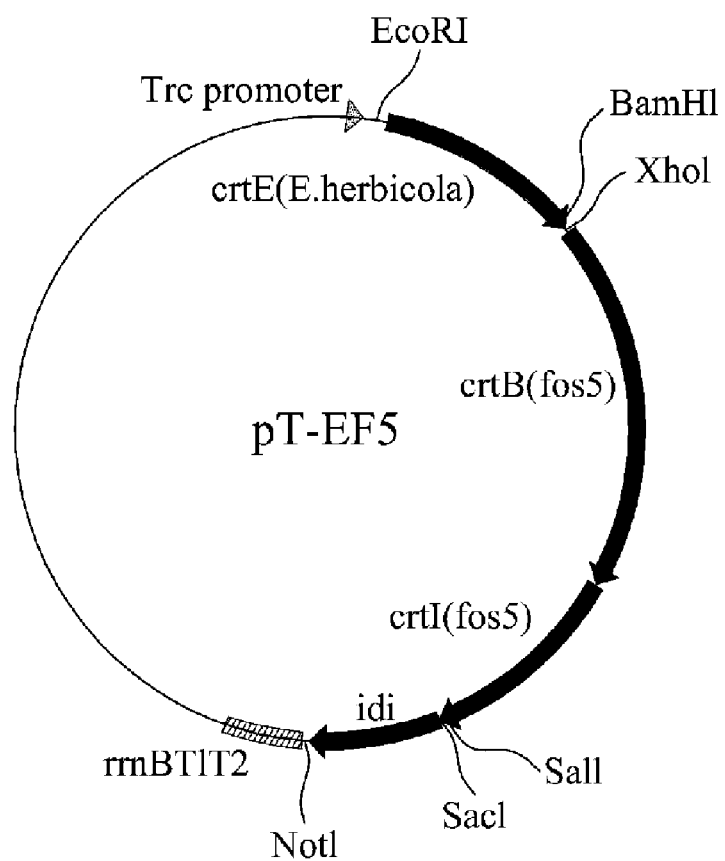

[Fig. 7]
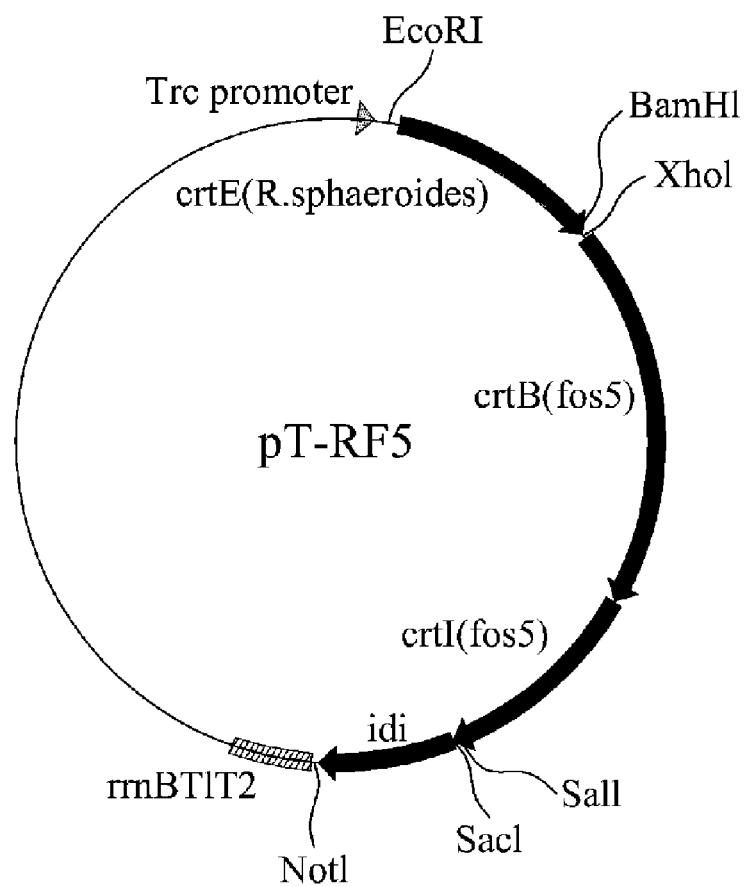

[Fig. 8]
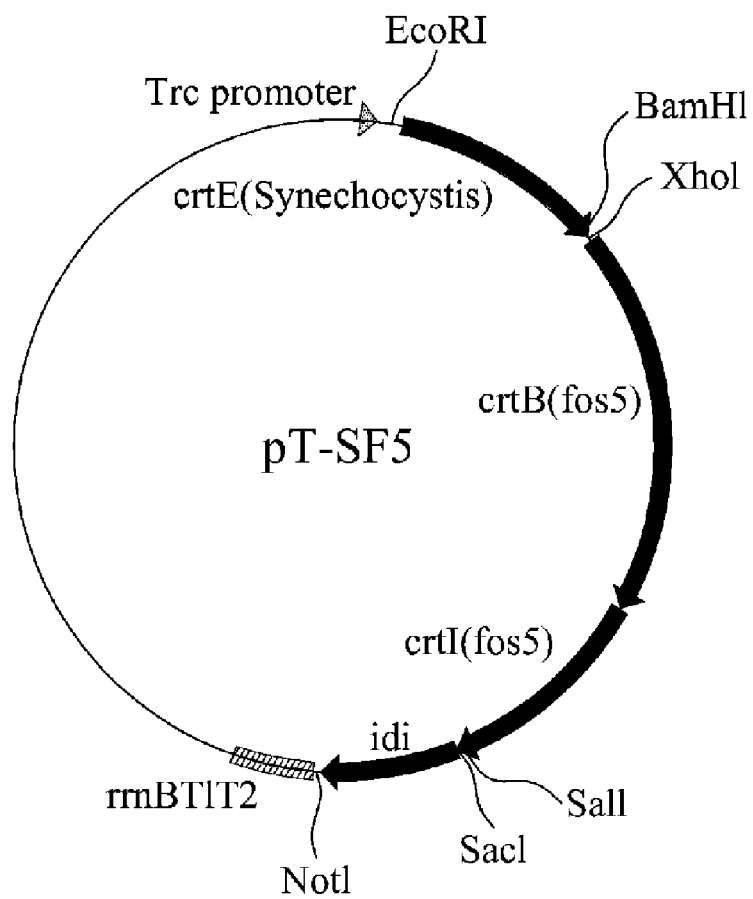

METHOD OF PRODUCING LYCOPENE USING RECOMBINANT *ESCHERICHIA COLI*

The present disclosure is the United States National Stage Entry of International Application No. PCT/KR2008/002535 having a filing date of May 6, 2008, which claims priority to Korean Patent Application No. 10-2007-0043682 having a filing date of May 4, 2007, which is incorporated herein in its entirety.

SEQUENCE LISTING

The instant application contains a Sequence Listing which has been submitted via EFS-Web and is hereby incorporated by reference in its entirety. Said ASCII copy, created on Mar. 16, 2010, is named CNS3PCUS.txt, and is 18,161 bytes in size.

TECHNICAL FIELD

The present invention relates to the method of producing highly concentrated lycopene by means of a bacterial strain that is transformed with a vector containing the genes encoding the proteins involved in lycopene biosynthesis. In more detail, the present invention relates to the method of producing lycopene with enhanced productivity, by culturing and fermenting transformed *E. coli*, under a specified condition, which has an introduced vector containing the genes required for lycopene biosynthesis, wherein the vector is prepared by combining at least one of the following new genes: crtE with the nucleotide Sequence 1, crtB with the nucleotide Sequence 3 and crtI with the nucleotide Sequence 5, of the Sequence List.

BACKGROUND ART

Lycopene has the structure shown in Chemical Structure 1, and can be obtained with a yield of 0.02 g from 1 kg of tomato. Lycopene, which is responsible for the red color of tomato, watermelon, grape, etc, is a lipid-soluble substance with very low polarity, and has strong antioxidant and anticancer effects.

As the excellent effects of carotenoids were proved as said, there has been increasing needs for lycopene. Lycopene has been produced by extraction directly from natural sources or by organic synthesis, while recently there have been researches actively going on to produce it by means of microorganism. Specifically there are two types of method which involve the cultivation and fermentation of microorganism to produce lycopene: (1) the method comprising the introduction of the genes which are required for lycopene biosynthesis into a bacterial strain which does not produce lycopene, (2) the method comprising the inactivation of lycopene cyclase of the bacterial strains which produce lycopene as an intermediate metabolic product of the biosynthesis of carotenoids such as carotene or astaxanthin.

The process of lycopene biosynthesis is illustrated in FIG. 1.

Glucose or glycerol are converted into isopentenyl pyrophosphate (hereafter IPP) or dimethylallyl pyrophosphate (hereafter DMAPP), via metabolic pathways such as 2-C-methyl-D-erythritol-4-phosphate pathway (hereafter MEP pathway) or the mevalonate pathway (hereafter MVA pathway). The present invention adopted MVA pathway for the biosynthesis of IPP. Via MVA pathway, glyceraldehyde-3-phosphate derived from glucose or glycerol is converted into Acetyl-CoA, which then undergoes a series of conversions into acetoacetyl-CoA, 3-hydroxy-3-methylglutaryl Coenzyme A (hereafter HMG-CoA), mevalonate, mevalonate-5-phosphate, mevalonate-5-diphosphate and eventually into IPP. The genes which encode the enzymes required for this process are atoB, mvaS, mvaA, mvaK1, mvaK2 and mvaD. The IPP thus synthesized undergoes a series of conversions to become farnesyl pyrophosphate (hereafter FPP), which is an important intermediate metabolic product of isoprenoid pathway. FPP is then converted into geranylgeranyl pyrophosphate (hereafter GGPP), which then into phytoene, which then finally converted into lycopene. The genes encoding the enzymes involved in this process are crtE, crtB and crtI.

As said, the mevalonate pathway and the non-mevalonate pathway are known as bio-synthetic pathways of IPP, which is a common precursor of carotenoids, and the mevalonate pathway is known to exist in most eukaryotes (e.g., *Saccha-*

[Chemical Structure 1]

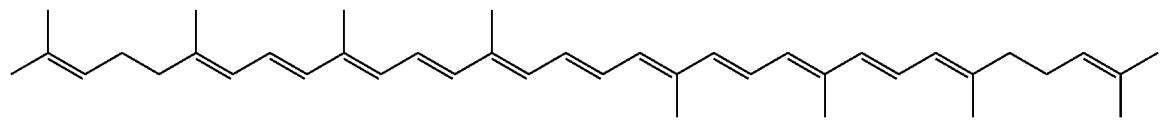

Hereunder is the summary of the previous studies about the art. In 2000, it was reported by Omer's group at the Carmanos Cancer institute in Detroit that lycopene suppressed the metastasis of prostate cancer (Omer Kucuk et al., Cancer Epidemiology, 10, 861-869, 2001). The effect of lycopene in releasing the symptom of patients with exercises-induced asthma was proved by the LycoRed, which is a specialized maker of lycopene, and by an allergy lab at the Hasharon hospital in Tel Aviv (I. Neuman et al., Allergy, 55, 1184-1189). Lycopene was also shown to have an excellent protective effect against myocardial disease and atherosclerosis, according to the clinical experiments carried out by the Research Institute of Public Health of the University of Cuopio in Finland. (Tiina Rissanen et al., Exp Biol Med (Maywood), 227, 900-907, 2002).

*romyces cerevisiae*), cytoplasm of plant cells, some bacteria (e.g., *Streptococcus pneumoniae* and *Paracoccus zeaxanthinifaciens*) and malarial cell. The non-mevalonate pathway exists in most bacteria (e.g., *E. coil*) and plastid of plant cells. Thus *E. coli*, which is a Gram-negative bacterium, biosynthesizes IPP only via the non-mevalonate pathway. Wild-type *E. coil*, however, has no genes required for the biosynthesis of carotenoids such as lycopene, and so can not produce lycopene.

As to the production of lycopene from the strains which does not produce lycopene, most studies have concerned either the finding of new genes involved in lycopene biosynthesis or the recombination of previously known genes, with a focus on the use of these genes for the biosynthesis of lycopene in *E. coli* or *Saccharomyces cerevisiae*. Roche Vitamins, Inc has made a strain of *E. coli* which has the lycopene content of 0.5 mg/gDCW by introducing crtB, crtI and crtE, which are the genes from Fla-vobacterium sp. R1534 (Luis Pasamontes and Yuri Tsygankov, US20040058410, 2004). Amoco Corporation has made a strain of *Saccharomyces cerevisiae* which has the lycopene content of 0.1 mg/gDCW, by using the crtI gene from *Erwinia herbicola* (Ausich, Rodney L. et al., U.S. Pat. No. 5,530,189, 1996). And Kirin Beer Kabushiki Kaisha has established a strain of *E. coli* which has the lycopene content of 2.0 mg/gDCW, by using the crtE, crtI and crtB genes from *Erwinia uredovora* (Narihiko Misawa et al., U.S. Pat. No. 5,429,939, 1995). Also a strain of transformed *Candida utilis* IFO 0988 with the lycopene content of 2.9 mg/gDCW was successfully prepared and cultured; which has the crtE, crtB and crtI genes from *Erwinia uredovora*, as well as the gene encoding HMG-CoA reductase of *Candida utilis* (Narihiko Misawa et al., J. of Biotechnology, 59, 169-181, 1998). Recently, a strain of recombinant *E. coil* obtained by transformation with crtE (encoding GGPP synthase), crtB (encoding phytoene synthase) and crtI (encoding phytoene desaturase), which are the carotenoid genes cloned from bacterial strains of *Agrobacterium aurantiacum, Erwinia herbicola* and *Erwinia uredovora*, has been reported to have the ability to biosynthesize lycopene (U.S. Pat. No. 6,706,516; Misawa and Shimada, J.Biotechnol., 59:169-181, 1998).

The yields of the studies, however, are very low, hindering the development of economical processes for lycopene production. To resolve this problem, the present invention employs new genes as well as combination of genes, providing the method of lycopene production with improved productivity using a transformed microorganism, wherein *E. coli* is transformed with atoB, mvaS, mvaA, mvaK1, mvaK2 and mvaD, which are the genes encoding the enzymes involved in the mevalonate pathway.

Thus the present invention is the result of the efforts to improve the lycopene productivity: For this, the crtE, crtB and crtI, which are some of the genes involved in lycopene biosynthesis, were isolated from sea metagenome and cloned, and their nucleotide sequences were determined; then the genes were introduced into vector in order to produce lycopene in a microorganism which does not produce lycopene, while the lycopen productivity was improved by combining new genes with previously known genes. In addition, lycopene productivity was further enhanced by introducing into *E. coli* the genes involved in the mevalonate pathway, thereby enabling *E. coli* to use the mevalonate pathway. Also a fermentation method was developed and provided to produce highly concentrated lycopene in the recombinant microorganism under a specified condition; the higher productivity of the strain than that of previous studies has been confirmed, and the present invention was accomplished thereupon.

DISCLOSURE OF INVENTION

Technical Problem

Accordingly, the present invention is directed to a method of producing lycopene efficiently from recombinant bacterial strain which is constructed using the recombinant vector containing new genes encoding the proteins required for lycopene biosynthesis.

According to an aspect of the present invention, the method of producing lycopene includes steps of preparing a recombinant vector containing genes encoding proteins, which are required for lycopene biosynthesis, wherein the genes involved in lycopen biosynthesis are crtE, crtB and crtI and at least one of the three genes (crtE, crtB and crtI) is selected from the group consisting of crtE with the nucleotide Sequence 1, crtB with the nucleotide Sequence 3 and crtI with the nucleotide Sequence 5, of the Sequence List; transforming the recombinant vector into *E. coli*; and culturing the *E. coli* transformant and recovering of lycopene from the culture medium.

Hereunder, the present invention will be described in more detail.

The present invention involves the cloning of crtE, crtB and crtI from sea metagenome, which are the 3 new genes encoding the proteins required for lycopene biosynthesis; the establishment of recombinant vector containing these genes; and the transformation with the recombinant vector of *E. coli* that does not produce lycopene.

Furthermore, the possibility of producing highly concentrated lycopene is proved by fermenting the *E. coli* which is transformed with the recombinant vector containing at least one of the new genes; preferably a combination of the new crtB (Sequence 3) and crtI (Sequence 5) genes with previously known crtE gene is proved to give higher productivity than that of previous studies; and thereupon the present invention has been accomplished.

The new genes of the present invention, each of which encoding a protein required for lycopene biosynthesis with a nucleotide sequence of either Sequence 1, Sequence 3 or Sequence 5, are obtained from sea metagenome. The Sequence 1, Sequence 2 and Sequence 3 encode following amino acid sequences, respectively: Sequence 2 (GGPP synthase), Sequence 4 (phytoene synthase) and Sequence 6 (phytoene desaturase).

The genes provided by the present invention may be transformed into a variety of host cells to be used usefully for lycopene production. Each of the new genes may be used separately, or more than 2 of them used together. For example, crtI of the present invention may be transformed into a microorganism which has only crtE and crtB to produce lycopene; also crtE, crtB and crtI of the present invention may be transformed into a microorganism which biosynthesizes carotenoids such as astaxanthin to attain better yield.

The present invention provides the method of producing lycopene in *E. coli* via the mevalonate pathway, by using lycopene biosynthesis genes along with the genes involved in the mevalonate pathway.

The method of the present invention comprising producing lycopene in microorganism using lycopene biosynthesis genes involves following 3 steps: (1) preparation of the recombinant vector which contains mvaK1, mvaD, mvaK2, mvaE, mvaS and idi in addition to the genes encoding the proteins required for lycopene biosynthesis, wherein the genes involved in lycopene biosynthesis are crtE, crtB and crtI and at least one of the three genes (crtE, crtB and crtI) is selected from the following group of genes: crtE with the nucleotide Sequence 1, crtB with the nucleotide Sequence 3 and crtI with the nucleotide Sequence 5, of the Sequence List; (2) trans-formation of the recombinant vector into *E. coli*; (3) culture of the *E. coli* transformant and recovering of lycopene from the culture medium.

The mvaK, mvaD, mvaK2, mvaE, mvaS, crtE, crtB, crtI and idi genes, which are required for the biosynthesis of lycopene, may be used for the construction of at least one or more than one separate vectors, wherein each vector contains at least one gene selected from the same genes; For example, each of mvaK, mvaD, mvaK2, mvaE, mvaS, crtE, crtB, crtI and idi genes may be either separately used to construct 9 vectors or to construct several vectors which contain at least one of the genes, to be used for transformation. The combination of the vectors, which are constructed separately, however, should be in such a way that the transformed *E. coli* has all the mvaK, mvaD, mvaK2, mvaE, mvaS, crtE, crtB, crtI and idi genes. The mvaE of the present disclosure is a gene which has functions of both atoB and mvaA in the process of lycopene biosynthesis shown in FIG. 2.

Preferably, vectors may be constructed separately so that one vector has mvaK, mvaD, mvaK2, mvaE and mvaS genes and the other has crtE, crtB, crtI and idi, to be transformed into *E. coli*; wherein, the mvaK, mvaD, mvaK2, mvaE and mvaS genes may be from previously known genes, while at least one of the crtE, crtB and crtI genes may be from sea metagenome.

As a preferred practice of the present invention, the recombinant vector containing crtE, crtB, crtI and idi genes has following genes: the crtE gene with Sequence 7, the crtB gene with Sequence 3, the crtI gene with Sequence 5 and the idi gene of *E. coli*. As another preferred practice of the present invention, the recombinant vector containing crtE, crtB, crtI and idi genes has following genes: the crtE gene with Sequence 8, the crtB gene with Sequence 3, the crtI gene with Sequence 5 and the idi gene of *E. coli*. As still another preferred practice of the present invention, the recombinant vector containing crtE, crtB, crtI and idi genes has following genes: the crtE gene from *Erwinia herbicola*, the crtB gene with Sequence 3, the crtI gene with Sequence 5 and the idi gene of *E. coli*.

The present invention is not limited to the combination of genes through the construction of certain types of recombinant vectors, but also includes any method of constructing a strain of *E. coli* that has mvaK, mvaD, mvaK2, mvaE, mvaS, crtE, crtB, crtI and idi genes, wherein at least one of crtE, crtB and crtI is the gene of the present invention obtained from sea metagenome.

In more detail, to produce highly concentrated lycopene from the culture of the recombinant strain, the basic culture conditions are optimized as follows: culture temperature is 25-35° C., pH of culture medium before autoclaving 7.0-7.5, shaking speed between 200 rpm and 1,000 rpm, and the concentration of dissolved oxygen between 20% and 30%.

On the other hand, the fed-batch culture is desirable to improve the growth of cells and the yield of lycopene. Culture medium is supplied whenever carbon sources are depleted; wherein the supply is controlled so that 0.4% of culture medium is added for each supply, and the composition of the culture medium is 70% of glycerol and 2% of $MgSO_4 \cdot H_2O$.

The amount of lycopene produced by the strain which is transformed according to the methods is measured for the present invention: That of the transformed *E. coli* which has the combination of the new crtE, crtB and crtI genes provided by the invention is 0.65 mg/L/hr; while that of the transformed *E. coli* which has the combination of at least one of the new genes of the invention with previously known genes is up to 3.30 mg/L/hr, which is increased to 9.7 mg/L/hr if fed-batch culture is employed, and to 36.5 mg/L/hr if additional IPTG induction is carried out.

In order to accomplish the object of the present invention, as described in detail: the mevalonate pathway was introduced; the optimum combination of genes was determined; fermentation condition was optimized through the fermentation of the recombinant *E. coli* prepared according to the method; and the higher productivity than that of previous inventions is established, providing an advantage over the previous inventions. The previous inventions give high yield but require much time, while the present invention gives high yield in a short time, making possible the development of economical process.

BRIEF DESCRIPTION OF THE DRAWINGS

FIG. 1 illustrates a process of lycopene biosynthesis.
FIG. 2 is the structure of recombinant vector pSANF.
FIG. 3 is the structure of recombinant vector pT5-ErEBI.
FIG. 4 is the structure of recombinant vector pT5-LYC-idi.
FIG. 5 is the structure of recombinant vector pT5-ErBI.
FIG. 6 is the structure of recombinant vector pT-EF5.
FIG. 7 is the structure of recombinant vector pT-RF5.
FIG. 8 is the structure of recombinant vector pT-SF5.

BEST MODE FOR CARRYING OUT THE INVENTION

The present invention is described in more detail with respect to examples hereunder. The examples hereunder, however, are only for the purpose of illustrating the present invention, and the scope of the present invention is not limited to the examples hereunder.

EXAMPLE 1

Cloning of the Genes Involved in the Lycopene Biosynthesis and the Preparation of the Recombinant Vector pSANF Wild-type *E. coli* does not produce lycopene, so mvaK1, mvaD, mvaK2, mvaE, mvaS, crtE, crtB, crtI and idi genes, which are involved in the production of mevalonate, IPP and lycopene, were introduced for lycopene production. Initially these genes were introduced into 2 vectors as follows: mvaK1, mvaD, mvaK2, mvaE and mvaS genes were introduced into pSTV28, while crtE, crtB, crtI and idi genes into pTrc99A. pSTV28 has the chloramphenicol resistance and pTrc99A the ampicillin resistance, so the recombinant strain containing both vectors together could be selected using both antibiotics.

Of those genes, mvaK1, mvaD, mvaK2, mvaE, mvaS and idi genes were from the genes whose sequences are already known, while crtB and crtI genes were selected from sea metagenome. The crtE gene from metagenome and that from previously known genes were separately used in order to measure lycopene productivity.

The mvaK1 gene was cloned from *Staphylococcus aureus* ATCC35556. The DNA fragment amplified from the genome DNA of *Staphylococcus aureus* ATCC35556 was digested with EcoRI and SacI, followed by insertion into pSTV28 vector that was digested at the same restriction sites, and the resulting recombinant vector was named pSTV28-SA1.

The mvaD and mvaK2 genes were cloned from the genome DNA of *Streptococcus pneumoniae*. The mvaD gene was digested with SacI and KpnI restriction enzymes, followed by insertion into pSTV28-SA1 vector that was digested at the same restriction sites, and the resulting recombinant vector was named pSTV28-SA1D. The mvaK2 gene was digested with KpnI and BamHI, followed by insertion into pSTV28-SA1D vector that was digested at the same restriction sites, and the resulting recombinant vector was named pSTV28-SA12D.

Before the insertion of mvaE and mvaS, the existence of promoter and transcription termination sequence were checked to carry out the over lap extension PCR, in order to join the DNA fragment containing the promoter with the DNA fragment containing the transcription termination sequence into a single fragment. The DNA fragment thus obtained was digested with BglII and NsiI, followed by insertion into pSTV28-SA12D vector that was digested with BamHI and PstI, and the resulting recombinant vector was named pSTV28-SA12D-Trc.

The mvaE and mvaS genes was cloned from the genome DNA of *Enterococcus faecalis* ATCC700802, and then subjected to the over lap extension PCR mvaE is a gene which functions as both atoB and mvaA in the process of lycopene biosynthesis. The DNA fragment containing mvaE and mvaS, which was obtained as said, was digested with BamHI and PstI, followed by insertion into pSTV28-SA12D-Trc vector that was digested at the same restriction sites, and the resulting recombinant vector was named pSANF <FIG. 2>.

The 5 genes were all purified with Qiagen PCR purification kit (Qiagen) before being used.

EXAMPLE 2

Cloning of the Genes Involved in the Lycopene Biosynthesis and the Construction of the Recombinant Vector pT5-LYC-idi 2.1 Cloning of crtE, crtB and crtI, which are the New Genes Involved in Lycopene Biosynthesis, from Sea Megagenome.

In order to obtain crtE, crtB and crtI, which are the genes involved in lycopene biosynthesis, genome DNA (metagenome) was obtained directly from the sea water and used to establish a library; and the clones with red color was selected taking an advantage of the red color of lycopene, followed by the DNA analysis of the clones.

To obtain metagenome DNA from sea, concentrated microorganisms were first obtained by concentrating large amount of sea water through membrane filtration. Since most microorganisms have the sizes between 0.2 µm and 10 µm, the large amount of sea water was initially passed through a filter with a pore size of 10 µm to remove various floating substances whose sizes are larger than 10 µm, and then the microorganisms whose sizes are lager than 0.2 µm are selectively collected using a filter with a pore size of 0.2 µm. Chromosomal DNA was isolated from the collected microorganisms by a method that uses CTAB (Hexadecyltrimethyl ammonium bromide) (Zhou et al., Appl. Environm. Microbiol. 62:316-322, 1996).

A library was constructed from the metagenome DNA which was obtained from the microorganisms, using a Copy Control fosmid library production kit (Epicenter) according to the manufacturer's manual. The kit used for library construction was Fosmid Vector Copy Control pCC1FOS (Epicenter). Ligation was carried out between the DNA to be inserted and the Copy Control vector pCC1FOS, and the ligated fosmid clones were subjected to packaging using the MaxPlax lambda packaging extracts (Epicenter). More than 10,000 clones could be obtained through the procedure.

The fosmid clones obtained as said was subjected to the stationary culture for 48 hours, then the color of the colonies was observed and red colonies selected. In order to check the existence of crt gene by PCR, primers were synthesized based on the conserved amino acid sequences in the C-terminus (crtIf) and the middle region of crtB (crtBr), of *Erwinia uredovora, Erwinia herbicola, Flavobacterium* sp. Strain ATCC21588, *Rhodobacter sphaeroides* and *Agrobacterium aurantiacum*. The nucleotide sequences of these primers are as follows:

```
crtIf:    5'-GTNGGNGCRGGCACNCAYCC-3'
crtBr:    5'-TCGCGRGCRATRTTSGTSARRTG-3'
```

The crt gene was amplified using the primers synthesized as said, while the template fosmid DNA was isolated from each of the red colonies. In detail, 100 ng of the fosmid DNA template was denatured at 94° C. for 5 minutes, followed by 20 cycles of 'at 94° C. for 30 seconds->at 50° C.~60° C. for 30 seconds->at 72° C. for 1 minute', then followed by 15 cycles of 'at 94° C. for 30 seconds->at 50° C. for 30 seconds->at 72° C. for 1 minute'. As a result, an expected band with a size of 620 by could be obtained from one colony, which was inserted into pST-Blue1 vector (Nwagen), and then subjected to nucleotide sequence analysis and was found to have a homology with the previously reported nucleotide sequence of crtB gene.

A cluster of the whole lycopene biosynthesis genes that includes the crtB gene was attempted to be obtained by means of southern blot, using the fragment of crtB gene obtained as said as a probe. The fragment of crtB used as a probe had a DIG compound attached by PCR, while the template DNA was digested with BamHI, SalI and EcoRI restriction enzymes before southern blot. The DNA treated with each of various restriction enzymes was first subjected to electrophoresis on 0.97% agarose gel to separate the fragments according to their sizes, which were then transferred to nitrocellulose membrane (Schelicher & Schuell, Germany) by capillary transfer method. Hybridization was performed at 42° C. for more than 6 hours in a standard solution containing 50% formamide (5×SSC, 0.1% N-Lauroylsarcosine, 0.02% SDS, 5% Blocking regent, 50% Formamide) with the probe added. The membrane was subjected to binding with an antibody against the DIG to which alkaline phosphotase is attached; then the substrates NBT and X-phosphate were added to induce color development according to the manual of the manufacturer (Boehringer-Mannheim, Germany).

A band with a size of about 4 kb among the EcoR1 fragment DNA which gave a signal upon southern blot was inserted into the pBluescript II KS(+) vector (Stratagene) for DNA sequence analysis. The sequence analysis proved that the band has a region of about 3.2 kb in total containing crtE, crtB and crtI.

As said, crtE, crtB and crtI genes were cloned from sea metagenome and have different nucleotide sequences from those of previously known genes. The idi gene encoding IPP isomerase was amplified from the genome DNA of *E. coli* MG1655.

2.2 Construction of Recombinant Vector pT5-LYC-idi

The DNA fragment containing the crtE gene obtained as said was first digested with EcoRI and BamHI, followed by insertion into the pTrc99A vector digested at the same restriction sites, and the resulting recombinant vector was named pT-f5crtE. A DNA fragment of about 2.4 kb which contains whole the crtB and crtI genes was obtained through the over lap extension PCR reaction, which was purified using the Qiagen PCR purification kit and then digested with XhoI and SalI, followed by insertion into pT-f5crtE digested at the same restriction sites, and the resulting recombinant vector was named pT-f5EBI. The idi gene from *E. coli* MG1655 was digested with Sad and NotI, followed by insertion into pT-f5EBI digested at the same restriction sites, and the resulting recombinant vector was named pT5-LYC-idi (FIG. 4).

All the genes were purified using the Qiagen PCR purification kit (Qiagen) before being used.

EXAMPLE 3

Evaluation of Lycopene Productivity of *E. coli* Transformed with the Vector which Contains a Combination of the crtE, crtB and crtI Genes from Sea Megagenome with the Mevalonate Synthesis Genes Lycopene biosynthesis was tested with the *E. coli* transformed with the pSANF and pT5-LYC-idi vectors of Example 1 and Example 2.

Initially MG1655 was transformed with the pSANF and pT5-LYC-idi vectors. A single colony of the transformed *E. coli* was obtained and inoculated into 5 mL of LB medium (10 g/L tryptone, 5 g/L yeast extract and 10 g/L NaCl) which contains 50 ppm of ampicillin and 20 ppm of chloramphenicol, followed by the shaking culture at 37° C. for 12 hours; then a 600 ml aliquot of the resulting culture medium was inoculated into 30 mL of 2YT medium which contains 1% of glycerol, 50 ppm of ampicillin and 20 ppm of chloramphenicol, followed by the main culture at 30° C. for 48 hours.

Upon the completion of the culture, an appropriate amount of the culture medium was taken to check lycopene productivity; by calculating dry cell weight (gDCW/L), yield (mg Lycopene/L, hereafter mg/L), content (mg Lycopene/gDCW, hereafter mg/gDCW) and productivity (mg Lycopene/L/hr, hereafter mg/L/hr).

In order to measure dry cell weight, 5 mL of the culture medium was taken and subjected to centrifugation in a 50 mL tube at 8,000 rpm for 10 minutes, and the cells were recovered by removing the supernatant. The recovered cells were suspended in 20 mL of sterilized distilled water and centrifuged to recover the cells that were cleansed of the components of the medium; then the recovered cells were completely suspended in 5 mL of sterilized distilled water and transferred to an aluminum weighing dish whose weight had been already measured. At this time, the centrifuge tube was washed with sterilized distilled water and the wash was added also to the weighing dish. The weighing dish was dried at 105° C. for more than 12 hours in a dry oven, followed by cooling, and then weighed to an accuracy of mg. Dry cell weight (gDCW/L) was calculated using Formula 1 below.

Dry Cell Weight(gDCW/L)={Weight of Dish with Dried Cells(mg)Weight of Dish(mg)}/5    [Formula 1]

The yield of lycopene was measured as follows: In order to extract lycopene, cells obtained from 100 µl of the culture medium by centrifugation was suspended in 400 µl of acetone, which was incubated at 55° C. for 15 minutes, which then 600 µl of acetone was added to and again incubated at 55° C. for 15 minutes. The extract was centrifuged at 14,000 rpm for 10 minutes, then the removed supernatant was measured of absorbance at the wavelength of 474.5 nm using a spectrophotometer. The measured value was substituted into an equation, which was obtained based on standard curve, to calculate the amount of lycopene based on the dilution rate. In order to obtain the standard curve, the standard lycopene purchased from Sigma was dissolved in acetone, the resulting solution was diluted to different concentrations of lycopene into acetone, and then the absorbances of the dilutes measured using a spectrophotometer at the wavelength of 474.5 nm was used to make the standard curve.

Lycopene Content (mg/gDCW) was calculated using Formula 2 based on the Dry Cell Weight and the Yield of lycopene.

Lycopene Content(mg/gDCW)=Yield of lycopene (mg/L)/Dry Cell Weight(gDCW/L)    [Formula 2]

Lycopene Productivity (mg/L/hr) was calculated using Formula 3, by dividing the Yield of lycopene, which was obtained as said, by incubation time.

Productivity(mg/L/hr)=Yield of lycopene(mg/L)/Incubation time(hr)    [Formula 3]

The Lycopene Productivity of the *E. coli* transformed with pSANF and pT5-LYC-idi, as determined according the method, is shown in Table 1.

Table 1

TABLE 1

| Dry Cell Weight (gDCW/L) | Yield (mg/L) | Content (mg/gDCW) | Productivity (mg/L/hr) |
|---|---|---|---|
| 5.11 | 31.2 | 6.1 | 0.65 |

EXAMPLE 4

Evaluation of Lycopene Productivity of *E. coli* Transformed with the Vector which Contains Either the crtE, crtB and crtI Genes from *Erwinia herbicola* or the Combination of the Genes with the Mevalonate Synthesis Genes 4.1 Evaluation of Lycopene Productivity of *E. coli* Transformed with the Vector which Contains the crtE, crtB and crtI Genes from *Erwinia herbicola*.

The crtE, crtB and crtI genes from *Erwinia herbicola* were obtained to construct pT5-ErEBI (FIG. 3), which was transformed into *E. coli* to evaluate lycopene productivity by the same method of Example 3. The lycopene productivity of the transformed *E. coli* measured after 48 hours of culture was shown in Table 2.

Table 2

TABLE 2

| Dry Cell Weight (gDCW/L) | Yield (mg/L) | Content (mg/gDCW) | Productivity (mg/L/hr) |
|---|---|---|---|
| 3.7 | 12.7 | 3.5 | 0.3 |

4.2 Evaluation of Lycopene Productivity of *E. coli* Transformed with the Vector which Contains the Combination of the crtE, crtB and crtI Genes from *Erwinia herbicola* with the Mevalonate Synthesis Genes.

The pT5-ErEBI containing the crtE, crtB and crtI genes from *Erwinia herbicola* and the pSANF of Example 1 were transformed into *E. coli* to evaluate lycopene productivity by the same method of Example 3. The lycopene productivity of the transformed *E. coli* measured after 48 hours of culture was shown in Table 3.

Table 3

TABLE 3

| Dry Cell Weight (gDCW/L) | Yield (mg/L) | Content (mg/gDCW) | Productivity (mg/L/hr) |
|---|---|---|---|
| 4.0 | 66.3 | 16.6 | 1.4 |

EXAMPLE 5

Evaluation of Lycopene Productivity of *E. coli* Transformed with the Vector which Contains the Combination of the crtE Gene from Sea Metagenome and the crtB and crtI Genes from *Erwinia herbicola* with the Mevalonate Synthesis Genes The crtB and crtI genes in the vector pT5-LYC-idi of the Example 2 were substituted by the already known same genes from *Erwinia herbicola* to construct recombinant vector pT5-ErBI (FIG. 5), which was transformed into *E. coli* to evaluate lycopene productivity by the same method of Example 3.

The lycopene productivity of the *E. coli* transformed with pSANF and pT5-ErBI measured after 48 hours of culture was shown in Table 4.

Table 4

TABLE 4

| Dry Cell Weight (gDCW/L) | Yield (mg/L) | Content (mg/gDCW) | Productivity (mg/L/hr) |
|---|---|---|---|
| 5.89 | 50.1 | 8.5 | 1.04 |

EXAMPLE 6

Evaluation of Lycopene Productivity of *E. coli* Transformed with the Vector which Contains the Combination of the crtE Gene from *Erwinia herbicola* (AMOCO CORPORATION, U.S. Pat. No. 5,530,189) and the crtB and crtI Genes from Sea Metagenome with the Mevalonate Synthesis Genes The crtE gene in the vector pT5-LYC-idi of the Example 2 was substituted by a same gene from *Erwinia herbicola* to construct recombinant vector pT-EF5 (FIG. 6), which was transformed into *E. coli* to evaluate lycopene productivity by the same method of Example 3.

The lycopene productivity of the *E. coli* transformed with pSANF and pT-EF5 measured after 48 hours of culture was shown in Table 5.

Table 5

TABLE 5

| Dry Cell Weight (gDCW/L) | Yield (mg/L) | Content (mg/gDCW) | Productivity (mg/L/hr) |
|---|---|---|---|
| 5.19 | 134.1 | 25.8 | 2.79 |

EXAMPLE 7

Evaluation of Lycopene Productivity of *E. coli* Transformed with the Vector which Contains the Combination of the crtE Gene from *Rhodobacter sphaeroides* (Sequence 7) and the crtB and crtI Genes from Sea Metagenome with Mevalonate Synthesis Genes The crtE gene in the vector pT5-LYC-idi of the Example 2 was substituted by a same gene from *Rhodobacter sphaeroides* to construct recombinant vector pT-RF5 (FIG. 7), which was transformed into *E. coli* to evaluate lycopene productivity by the same method of Example 3.

The lycopene productivity of the *E. coli* transformed with pSANF and pT-RF5 was shown in Table 6.

Table 6

TABLE 6

| Dry Cell Weight (gDCW/L) | Yield (mg/L) | Content (mg/gDCW) | Productivity (mg/L/hr) |
|---|---|---|---|
| 5.63 | 106.4 | 18.9 | 2.22 |

EXAMPLE 8

Evaluation of Lycopene Productivity of *E. coli* Transformed with the Vector which Contains the Combination of the crtE Gene from *Synechocystis* sp. PCC6803 (Sequence 8) and the crtB and crtI Genes from Sea Metagenome with the Mevalonate Synthesis Genes The crtE gene in the vector pT5-LYC-idi of the Example 2 was substituted by a same gene from *Synechocystis* sp. PCC6803 to construct recombinant vector pT-SF5 (FIG. 8), which was transformed into *E. coli* to evaluate lycopene productivity by the same method of Example 3.

The lycopene productivity of the *E. coli* transformed with pSANF and pT-SF5 was shown in Table 7.

Table 7

TABLE 7

| Dry Cell Weight (gDCW/L) | Yield (mg/L) | Content (mg/gDCW) | Productivity (mg/L/hr) |
|---|---|---|---|
| 4.52 | 158.2 | 35.0 | 3.30 |

EXAMPLE 9

Evaluation of Lycopene Productivity of the Fed-Batch Cultured *E. coli* Transformed with the Vector which Contains the Combination of the crtE Gene from *Synechocystis* sp. PCC6803 and the crtB and crtI Genes from Sea Metagenome with Mevalonate Synthesis Genes The *E. coli* transformed with the pSANF and pT-SF5 of Example 8 was subjected to the fed-batch culture.

A Biostat B fermenter (B. Brown Biotech International) was used for the fed-batch culture. The total volume of the medium container was 5 L, and the working volume was 2 L.

The fermenter was equipped with a pH meter to monitor proton concentration, a DO meter to monitor the concentration of dissolved oxygen, and a foam sensor which can detect foams in order to remove the foams appearing during the fermentation.

During the fermentation, pH was controlled with ammonia solution and 30% phosphoric acid, and the compressed air being injected into the fermenter was controlled to maintain the flow rate of 2 L/min. The temperature of the fermenter was kept at 30° C., while appropriate maintenance was made to keep the shaking speed between 200 rpm and 1,000 rpm and the concentration of dissolved oxygen between 20% and 30%. The fermenter contained 2 L of sterilized culture median for lycopene production. The culture median used for lycopene production was the modified Kortz culture median (D. J. Korz et al., J. of Biotechnology, 39, 59-65, 1995), whose pH was adjusted to 7.0 prior to autoclaving, and whose composition was as follows: glycerol 2%, $KH_2PO_4$ 1.33%, $(NH_4)_2HPO_4$ 0.4%, $MgSO_4.7H_2O$ 0.12%, citric acid 0.17%, EDTA 8.4 mg/L, $CoCl_2.6H_2O$ 2.5 mg/L, $MnCl_2.4H_2O$ 15.0 mg/L, $CuCl_2.2H_2O$ 1.5 mg/L, $H_3BO_3$ 3.0 mg/L, $Na_2MoO_4.2H_2O$ 2.5 mg/L, $Zn(CH_3COO)_2.2H_2O$ 13.0 mg/L, and Fe(III) citrate 100 mg/L. The fermenter containing the culture medium was autoclaved at 121° C. for 15 minutes to sterilize the fermenter of any microorganism inside, and then the antibiotics ampicillin and chloramphenicol were added to the concentrations of 50 ppm and 20 ppm, respectively, prior to inoculation.

The colony of Example 8 was inoculated into 3 mL of LB medium in a test tube using a platinum loop, followed by the first preincubation in a shaking fermenter at 30° C. When the optical density (hereafter O.D.) reached around 1.0 during the culture, as measured by a spectrophotometer at 600 nm, a 2 mL aliquot of the culture medium was taken and inoculated into 100 mL of fresh culture medium in a 500 mL Erlenmeyer flask. The inoculated culture medium was subjected to the second preincubation at 30° C., which was then, when the O.D. reached 1.0 again, inoculated into the whole medium in the autoclaved fermenter for the fed-batch culture. During the culture, whenever carbon sources were depleted, nutrients were supplied by adding 0.4% of culture medium for each supply; the culture medium was composed of 70% glycerol and 2% MgSO4.7H2O.

At several time points with regular intervals during the culture, an aliquot of the culture medium was taken to measure the O.D. and the yield (mg/L). The lycopene productivity measured after 48 hours of culture was shown in Table 8.

Table 8

TABLE 8

| Dry Cell Weight (gDCW/L) | Yield (mg/L) | Content (mg/gDCW) | Productivity (mg/L/hr) |
|---|---|---|---|
| 39.8 | 466 | 11.7 | 9.7 |

EXAMPLE 10

Enhancement of Lycopene Productivity by IPTG Induction

The colony of Example 8 was inoculated into 3 mL of LB medium in a test tube using a platinum loop, followed by the first preincubation in a shaking fermenter at 30° C. When the O.D. reached around 1.0 during the culture, as measured by a spectrophotometer at 600 nm, a 2 mL aliquot of the culture medium was taken and inoculated into 100 mL of fresh culture medium in a 500 mL Erlenmeyer flask. The inoculated culture medium was subjected to the second preincubation at 30° C., which was then, when the O.D. reached 1.0 again, inoculated into the whole medium in the autoclaved fermenter for the fed-batch culture by the same method as in Example 9.

At several time points with regular interval during the culture, an aliquot of the culture medium was taken to measure the O.D. and the yield (mg/L). When the O.D. reached 70.0, as measured by a spectrophotometer at 600 nm, IPTG induction was carried out at concentration of 0.025 mM. The lycopene productivity measured after 48 hours of culture was shown in Table 9.

Table 9

TABLE 9

| Dry Cell Weight (gDCW/L) | Yield (mg/L) | Content (mg/gDCW) | Productivity (mg/L/hr) |
|---|---|---|---|
| 46.1 | 1754 | 38.1 | 36.5 |

The crtE, crtB and crtI genes may be used for lycopene production either alone or through the combination of at least one of them with previously known genes; while the recombinant strain which contains the combination of genes of the present invention was able to give improved productivity compared to that of previously known inventions. In addition, the lycopene productivity could be further enhanced by introducing the genes required for the mevalonate pathway so that lycopene could be produced via the mevalonate pathway in *E. coli*. Therefore, the present invention can be very usefully applied to mass production of lycopene, for which there are increasing needs recently due to its antioxidant activity and the anticancer effect.

Sequence Listing

Sequence 1 is the nucleotide sequence of the gene crtE (867 bp) from sea metagenome.

Sequence 2 is the amino acid sequence of geranylgeranyl pyrophosphate synthase (288 amino acids) encoded by the gene crtE.

Sequence 3 is the nucleotide sequence of the gene crtB (909 bp) from sea metagenome.

Sequence 4 is the amino acid sequence of phytoene synthase (302 amino acids) encoded by the gene crtB.

Sequence 5 is the nucleotide sequence of the gene crtI (1,485 bp) from sea metagenome.

Sequence 6 is the amino acid sequence of phytoene desaturase (494 amino acids) encoded by the gene crtI.

Sequence 7 is the nucleotide sequence of the gene crtE of *Rhodobacter sphaeroides*.

Sequence 8 is the nucleotide sequence of the gene crtE of *Synechocystis* sp. PCC 6803.

The invention claimed is:

1. A method of producing lycopene comprising:
preparing a recombinant vector containing genes encoding proteins, which are required for lycopene biosynthesis, wherein the genes involved in lycopene biosynthesis are one or more of crtE with the nucleotide SEQ ID NO.: 1, crtB with the nucleotide SEQ ID NO.:3 and crtI with the nucleotide SEQ ID NO.:5;
transforming the recombinant vector into E. coli; and
culturing the E. coli transformant and recovering lycopene from the culture medium.

2. The method of claim 1, wherein the recombinant vector further comprises one or more of mvaK1, mvaD, mvaK2, mvaE, mvaS and idi in addition to the genes involved in lycopene biosynthesis.

3. The method of claim 2, wherein the idi gene is idi of E. coli.

4. The method of, claim 1 wherein the transformant is cultured under the following conditions: culture temperature ranging from 25° C. to 35° C., pH of culture medium before autoclaving ranging from 7.0 to 7.5, shaking speed ranging from 200 rpm to 1,000 rpm, and the concentration of dissolved oxygen ranging from 20% to 30%.

5. The method of claim 1 wherein the transformant is cultured by a fed-batch culture for mass production of lycopene.

* * * * *

SEQUENCE LISTING

```
<160> NUMBER OF SEQ ID NOS: 10

<210> SEQ ID NO 1
<211> LENGTH: 867
<212> TYPE: DNA
<213> ORGANISM: Unknown
<220> FEATURE:
<223> OTHER INFORMATION: Description of Unknown: crtE of meta genome
      from sea water

<400> SEQUENCE: 1
```

```
atgataagcc ctatatccac tgctgatgtg gcctttgagc gcctcgttga cagctgtgaa    60
cgatcgttga aagagtgtat agccgcgagc tgtccagccc ttcatcaagc ttggcagcat   120
cagttcgcag cgcgaggcaa gcgtttacgt atgcacctag ccttagaaag tagtctggcg   180
ctagggttga ccgaccatca atgccacacc attgcggtgg catgcgaatt agtccaccag   240
gcctcattga ttcacgatga tgtgcttgat gcggataccc accgaaatgg caaagcaacg   300
gtttggcacc agtatggagc tgccacagca atttgtctgg gtgacagttt attagttgag   360
gcaatgctgc aaatagcgtt gttggaaaat ttaccgagcg ccgttcggca gcagcttgtg   420
caattattta agatgccat acaagccgcc gctgagggcc aaattgacga ttgtaatagc   480
gacaaaatag ccaactatag ccatgccgat tattgcactg cagtgcgcaa aaaatcaggc   540
gcgctgttcg gcttaccggt gttggcggct atgttaatga gtcaacagca tgcaattact   600
atcggggtag ccaaccgagc ctatgctgaa tttggtattg cctatcagtt actcgatgac   660
ctgcatgacc gtgacgttga tcagcagggt cggatgaacg ttattgggt attaagtcgg   720
gattatccga ccggggtaga agcagcactc tttgctgcgg ttgagcagca tctcggcgag   780
gccgagcgac tgatcgcatc attgccatcg agcttgcacc ccagctttta tgtggtgcat   840
gactcgctcc gagcgaagct cccatga                                        867
```

<210> SEQ ID NO 2
<211> LENGTH: 288
<212> TYPE: PRT
<213> ORGANISM: Unknown
<220> FEATURE:
<223> OTHER INFORMATION: Description of Unknown: Geranylgeranyl
      Pyrophosphate Synthase

<400> SEQUENCE: 2

Met Ile Ser Pro Ile Ser Thr Ala Asp Val Ala Phe Glu Arg Leu Val
1               5                   10                  15

Asp Ser Cys Glu Arg Ser Leu Lys Glu Cys Ile Ala Ala Ser Cys Pro
            20                  25                  30

Ala Leu His Gln Ala Trp Gln His Gln Phe Ala Ala Arg Gly Lys Arg
        35                  40                  45

Leu Arg Met His Leu Ala Leu Glu Ser Ser Leu Ala Leu Gly Leu Thr
    50                  55                  60

Asp His Gln Cys His Thr Ile Ala Val Ala Cys Glu Leu Val His Gln
65                  70                  75                  80

Ala Ser Leu Ile His Asp Asp Val Leu Asp Ala Asp Thr His Arg Asn
                85                  90                  95

Gly Lys Ala Thr Val Trp His Gln Tyr Gly Ala Ala Thr Ala Ile Cys
            100                 105                 110

Leu Gly Asp Ser Leu Leu Val Glu Ala Met Leu Gln Ile Ala Leu Leu
        115                 120                 125

Glu Asn Leu Pro Ser Ala Val Arg Gln Gln Leu Val Gln Leu Phe Lys
    130                 135                 140

Asp Ala Ile Gln Ala Ala Ala Glu Gly Gln Ile Asp Asp Cys Asn Ser
145                 150                 155                 160

Asp Lys Ile Ala Asn Tyr Ser Tyr Ala Asp Tyr Cys Thr Ala Val Arg
                165                 170                 175

Lys Lys Ser Gly Ala Leu Phe Gly Leu Pro Val Leu Ala Ala Met Leu
            180                 185                 190

Met Ser Gln Gln His Ala Ile Thr Ile Gly Val Ala Asn Arg Ala Tyr
        195                 200                 205

-continued

```
Ala Glu Phe Gly Ile Ala Tyr Gln Leu Leu Asp Asp Leu His Asp Arg
            210                 215                 220
Asp Val Asp Gln Gln Gly Arg Met Asn Gly Tyr Trp Val Leu Ser Arg
225                 230                 235                 240
Asp Tyr Pro Thr Gly Val Glu Ala Ala Leu Phe Ala Ala Val Glu Gln
                245                 250                 255
His Leu Gly Glu Ala Glu Arg Leu Ile Ala Ser Leu Pro Ser Ser Leu
            260                 265                 270
His Pro Ser Phe Tyr Val Val His Asp Ser Leu Arg Ala Lys Leu Pro
        275                 280                 285
```

<210> SEQ ID NO 3
<211> LENGTH: 909
<212> TYPE: DNA
<213> ORGANISM: Unknown
<220> FEATURE:
<223> OTHER INFORMATION: Description of Unknown: crtB of meta genome
      from sea water

<400> SEQUENCE: 3

| | | |
|---|---|---|
| atgaagatag cgctggaccg gcctgagcat gctgccatta tgcagcagca tggcaagtca | 60 |
| ttttatttgg ctggtagctt tctcggtcgt gatgcctggc agcgtgcgtc agcgctttat | 120 |
| gcttttttac gccatatcga cgaccaaatt gatgaagctg aaacatctgc cgtagcagcg | 180 |
| caacgactgg cacagattcg tcagcagctg ttctcaagcg caatcatgac cgacgcagat | 240 |
| gagcagagct taagcattga gcaaagcacc ctggagcaat ttttgcgtgg catggcttat | 300 |
| gacattggtc acgttgctat tgctgatcag gctgagttag aagactactg ctattgtgtc | 360 |
| gccggcaccg tcggtgaaat gatgtgtcag gccttgcgct gtgatgaccc gcgcgcaatt | 420 |
| ggtcatgcta ttgatttggg tgtcgctatg caaatgacca atattgcccg cgatgttcat | 480 |
| gccgatagcg ccttagggcg ccgttatttta cccgccacct gggttggtga tctcagtgct | 540 |
| gagagcatta ccacggcaac accagctatc tcggcacaga tagccgcggc aattatgcgg | 600 |
| ctgattgcgt tatctgagca gcgttatcaa tcagcgtatg cgggtatcgc actgttgccg | 660 |
| ttgcgctcgc gcttggcaat tttggcggca agtcaccttt atgccggtat tggtcgcgcc | 720 |
| attgcggcgg agcatgcgca atcatggcag caacggaagg tgttgtcagg gtcgcgtaag | 780 |
| gcggcaatta ctgccgccgc agtggcggaa tttgcgactc gaccgcgact atggcgttat | 840 |
| tacgcgcagc ctagcttcgg taagccggcc gagcggatcg ctgcgtctgt tggcagtgag | 900 |
| ggtttatga | 909 |

<210> SEQ ID NO 4
<211> LENGTH: 302
<212> TYPE: PRT
<213> ORGANISM: Unknown
<220> FEATURE:
<223> OTHER INFORMATION: Description of Unknown: Phytoene Synthase

<400> SEQUENCE: 4

```
Met Lys Ile Ala Leu Asp Arg Pro Glu His Ala Ala Ile Met Gln Gln
1               5                   10                  15
His Gly Lys Ser Phe Tyr Leu Ala Gly Ser Phe Leu Gly Arg Asp Ala
            20                  25                  30
Trp Gln Arg Ala Ser Ala Leu Tyr Ala Phe Leu Arg His Ile Asp Asp
        35                  40                  45
Gln Ile Asp Glu Ala Glu Thr Ser Ala Val Ala Ala Gln Arg Leu Ala
    50                  55                  60
```

```
Gln Ile Arg Gln Gln Leu Phe Ser Ala Ile Met Thr Asp Ala Asp
 65                  70                  75                  80

Glu Gln Ser Leu Ser Ile Glu Gln Ser Thr Leu Glu Gln Phe Leu Arg
                 85                  90                  95

Gly Met Ala Tyr Asp Ile Gly His Val Ala Ile Ala Asp Gln Ala Glu
            100                 105                 110

Leu Glu Asp Tyr Cys Tyr Cys Val Ala Gly Thr Val Gly Glu Met Met
        115                 120                 125

Cys Gln Ala Leu Arg Cys Asp Asp Pro Arg Ala Ile Gly His Ala Ile
    130                 135                 140

Asp Leu Gly Val Ala Met Gln Met Thr Asn Ile Ala Arg Asp Val His
145                 150                 155                 160

Ala Asp Ser Ala Leu Gly Arg Arg Tyr Leu Pro Ala Thr Trp Val Gly
                165                 170                 175

Asp Leu Ser Ala Glu Ser Ile Thr Thr Ala Thr Pro Ala Ile Ser Ala
            180                 185                 190

Gln Ile Ala Ala Ala Ile Met Arg Leu Ile Ala Leu Ser Glu Gln Arg
        195                 200                 205

Tyr Gln Ser Ala Tyr Ala Gly Ile Ala Leu Leu Pro Leu Arg Ser Arg
    210                 215                 220

Leu Ala Ile Leu Ala Ala Ser His Leu Tyr Ala Gly Ile Gly Arg Ala
225                 230                 235                 240

Ile Ala Ala Glu His Ala Gln Ser Trp Gln Gln Arg Lys Val Leu Ser
                245                 250                 255

Gly Ser Arg Lys Ala Ala Ile Thr Ala Ala Ala Val Ala Glu Phe Ala
            260                 265                 270

Thr Arg Pro Arg Leu Trp Arg Tyr Tyr Ala Gln Pro Ser Phe Gly Lys
        275                 280                 285

Pro Ala Glu Arg Ile Ala Ala Ser Val Gly Ser Glu Gly Leu
    290                 295                 300

<210> SEQ ID NO 5
<211> LENGTH: 1485
<212> TYPE: DNA
<213> ORGANISM: Unknown
<220> FEATURE:
<223> OTHER INFORMATION: Description of Unknown: crtI of meta genome
      from sea water

<400> SEQUENCE: 5
atgcaaacag ttgttattgg tggaggctta ggtggtatcg cagcggcgtt gcgagcccgt      60
gcaaaaggcc atcaagtcac cctaatagaa aaaatcagc agttaggtgg ccgtgcgcaa     120
gtatttgaac gtgagggttt tcgtttttgat gccggcccca ccgtgattac tgcaccattc    180
ttgtttgatg agctatttga attatttggc aaaaaacgcc aagactatgt cgagtttatt    240
ccgctcaatc cgtggtacca attttactac agtgacgaca gtcgcgctt caactatggt    300 ggaagtgtcg atgacacctt gcaagaaatt gctaaaattg agccaagtga ccaggccaat    360
tatctgcgtt taatcgagca tagcaaaaag atctacaaaa tcggctttga gcaactcgcc    420
gatcagccgt tcacaagct ttccaccatg ttaaagcaaa ttccccattt gggccggctg    480
cgcgctgacc gcacggtttg gaatatggtt agtcgctatc ttaaaaatga caaactacgc    540
caagcttttt ctattcagtc attgctagta ggtggtaacc catttgatac caccagtatt    600
tatggactga ttcattattt agagcgggaa tatggcattc atttcgccat gggcggcacc    660
ggtgccatta ttgatgcatt acacaagctg atgctcgaag agggtatcga ggtgcgcacg    720
```

```
aactgctgtg tcaccgactt tcatagcagc ccgagccgca ttgagagcgc agtgattaat    780
cagcacgagg tgctatctgc tgactacttt attttttaatg gcgacccact gtatttgtat    840
aaacacctgt tacctgaaag ttctgctaat ttgcaattac ggttgaaggt tgatcacagt    900
aaacgctcaa tgggtctata tgtgctgttt tttggcacca ccaaacaata tccagaggtt    960
gagcatcaca ctatttggct gggcaagcgt tatcagcaat tattagcaga aatttttgcc   1020
gaaaaatcat acccgatga ttttcactt tatgtacata gaccaactgc ttcggatcca   1080
tcctttgcgc cggctggttg cgacagcttt tatgtgttag ctccggtgcc caatctgcgg   1140
gcagatatag attggcaggt tgaggaaccc aagttgcgac aacggatcat cgacgcgcta   1200
gcagatacct tattgccggg cttacatgac tgtattaccg ctgagtttgc gatgacccca   1260
gaacagttta aaagcgatta tttgagtgtc gatggcgctg gcttttccat tgcacccaaa   1320
tttactcagt cggcgtggtt ccgttttcat aatctgtcgg aaaaatatag caacttatta   1380
ctcgctggtg ccgaacgca cccaggtgct ggcatgccgg gcgtactctg ttcggcaaaa   1440
gtcattgaaa aactgctccc tgtggtgact gcggagcagc catga                    1485
```

<210> SEQ ID NO 6
<211> LENGTH: 494
<212> TYPE: PRT
<213> ORGANISM: Unknown
<220> FEATURE:
<223> OTHER INFORMATION: Description of Unknown: Phytoene Desaturase

<400> SEQUENCE: 6

```
Met Gln Thr Val Val Ile Gly Gly Leu Gly Ile Ala Ala Ala
1               5                   10                  15

Leu Arg Ala Arg Ala Lys Gly His Gln Val Thr Leu Ile Glu Lys Asn
            20                  25                  30

Gln Gln Leu Gly Gly Arg Ala Gln Val Phe Glu Arg Glu Gly Phe Arg
        35                  40                  45

Phe Asp Ala Gly Pro Thr Val Ile Thr Ala Pro Phe Leu Phe Asp Glu
    50                  55                  60

Leu Phe Glu Leu Phe Gly Lys Lys Arg Gln Asp Tyr Val Glu Phe Ile
65                  70                  75                  80

Pro Leu Asn Pro Trp Tyr Gln Phe Tyr Tyr Ser Asp Asp Lys Ser Arg
                85                  90                  95

Phe Asn Tyr Gly Gly Ser Val Asp Asp Thr Leu Gln Glu Ile Ala Lys
            100                 105                 110

Ile Glu Pro Ser Asp Gln Ala Asn Tyr Leu Arg Leu Ile Glu His Ser
        115                 120                 125

Lys Lys Ile Tyr Lys Ile Gly Phe Glu Gln Leu Ala Asp Gln Pro Phe
    130                 135                 140

His Lys Leu Ser Thr Met Leu Lys Gln Ile Pro His Leu Gly Arg Leu
145                 150                 155                 160

Arg Ala Asp Arg Thr Val Trp Asn Met Val Ser Arg Tyr Leu Lys Asn
                165                 170                 175

Asp Lys Leu Arg Gln Ala Phe Ser Ile Gln Ser Leu Leu Val Gly Gly
            180                 185                 190

Asn Pro Phe Asp Thr Thr Ser Ile Tyr Gly Leu Ile His Tyr Leu Glu
        195                 200                 205

Arg Glu Tyr Gly Ile His Phe Ala Met Gly Gly Thr Gly Ala Ile Ile
    210                 215                 220

Asp Ala Leu His Lys Leu Met Leu Glu Glu Gly Ile Glu Val Arg Thr
225                 230                 235                 240
```

Asn Cys Cys Val Thr Asp Phe His Ser Ser Pro Ser Arg Ile Glu Ser
              245                 250                 255

Ala Val Ile Asn Gln His Glu Val Leu Ser Ala Asp Tyr Phe Ile Phe
          260                 265                 270

Asn Gly Asp Pro Leu Tyr Leu Tyr Lys His Leu Leu Pro Glu Ser Ser
      275                 280                 285

Ala Asn Leu Gln Leu Arg Leu Lys Val Asp His Ser Lys Arg Ser Met
  290                 295                 300

Gly Leu Tyr Val Leu Phe Phe Gly Thr Thr Lys Gln Tyr Pro Glu Val
305                 310                 315                 320

Glu His His Thr Ile Trp Leu Gly Lys Arg Tyr Gln Gln Leu Leu Ala
              325                 330                 335

Glu Ile Phe Ala Glu Lys Ser Leu Pro Asp Asp Phe Ser Leu Tyr Val
          340                 345                 350

His Arg Pro Thr Ala Ser Asp Pro Ser Phe Ala Pro Ala Gly Cys Asp
      355                 360                 365

Ser Phe Tyr Val Leu Ala Pro Val Pro Asn Leu Arg Ala Asp Ile Asp
  370                 375                 380

Trp Gln Val Glu Glu Pro Lys Leu Arg Gln Arg Ile Ile Asp Ala Leu
385                 390                 395                 400

Ala Asp Thr Leu Leu Pro Gly Leu His Asp Cys Ile Thr Ala Glu Phe
              405                 410                 415

Ala Met Thr Pro Glu Gln Phe Lys Ser Asp Tyr Leu Ser Val Asp Gly
          420                 425                 430

Ala Gly Phe Ser Ile Ala Pro Lys Phe Thr Gln Ser Ala Trp Phe Arg
      435                 440                 445

Phe His Asn Leu Ser Glu Lys Tyr Ser Asn Leu Leu Ala Gly Ala
  450                 455                 460

Gly Thr His Pro Gly Ala Gly Met Pro Gly Val Leu Cys Ser Ala Lys
465                 470                 475                 480

Val Ile Glu Lys Leu Leu Pro Val Val Thr Ala Glu Gln Pro
              485                 490

<210> SEQ ID NO 7
<211> LENGTH: 867
<212> TYPE: DNA
<213> ORGANISM: Rhodobacter sphaeroides
<220> FEATURE:
<223> OTHER INFORMATION: crtE sequence

<400> SEQUENCE: 7
atggcgtttg aacagcggat tgaagcggca atggcagcgg cgatcgcgcg gggccagggc      60
tccgaggcgc cctcgaagct ggcgacggcg ctcgactatg cggtgacgcc cggcggcgcg     120
cgcatccggc ccacgcttct gctcagcgtg gccacgcgct gcggcgacag ccgcccggct     180
ctgtcggacg cggcggcggt ggcgcttgag ctgatccatt gcgcgagcct cgtgcatgac     240
gatctgccct gcttcgacga tgccgagatc cggcgcggca agcccacggt gcatcgcgcc     300
tattccgagc cgctggcgat cctcaccggc gacagcctga tcgtgatggg cttcgaggtg     360
ctggccggcg ccgcggccga ccgaccgcag cgggcgctgc agctggtgac ggcgctggcg     420
gtgcggacgg ggatgccgat gggcatctgc gcggggcagg gctgggagag cgagagccag     480
atcaatctct cggcctatca tcgggccaag accggcgcgc tcttcatcgc cgcgacccag     540
atgggcgcca ttgccgcggg ctacgaggcc gagccctggg aagagctggg agcccgcatc     600
ggcgaggcct tccaggtggc cgacgacctg cgcgacgcgc tctgcgatgc cgagacgctg     660

```
ggcaagcccg cggggcagga cgagatccac gcccgcccga gcgcggtgcg cgaatatggc      720
gtcgagggcg cggcgaaggg gctgaaggac atcctcggcg gcgccatcgc ctcgatcccc      780
tcctgcccgg ccgaggcgat gctggccgag atggtccgcc gctatgccga caagatcgtg      840
ccggcgcagg tcgcggcccg cgtctga                                         867
```

```
<210> SEQ ID NO 8
<211> LENGTH: 909
<212> TYPE: DNA
<213> ORGANISM: Synechocystis sp.
<220> FEATURE:
<223> OTHER INFORMATION: crtE sequence (PCC 6803)

<400> SEQUENCE: 8
```

```
atggttgccc aacaaacacg aaccgacttt gatttagccc aatacttaca agttaaaaaa      60
ggtgtggtcg aggcagccct ggatagttcc ctggcgatcg cccggccgga aaagatttac     120
gaagccatgc gttattctct gttggcgggg ggcaaacgat gcgaccgat tttatgcatt      180 acggcctgcg aactgtgtgg cggtgatgaa gccctggcct tgcccacggc ctgtgccctg     240
gaaatgatcc acaccatgtc cctcatccat gatgatttgc cctccatgga taatgacgat     300
ttccgccggg gtaaacccac taaccacaaa gtgtacgggg aagacattgc cattttggcc     360
ggggatggac tgctagccta tgcgtttgag tatgtagtta cccacacccc ccaggctgat     420
ccccaagctt tactccaagt tattgcccgt ttgggtcgca cggtggggc cgccggttta     480 gtgggggac aagttctaga cctggaatcg gaggggcgca ctgacatcac cccggaaacc     540
ctaactttta tccatacccca taaaaccggg gcattgctgg aagcttccgt gctcacaggc     600
gcaattttgg ccggggccac tggggaacaa caacagagac tggcccgcta tgcccagaat     660
attggcttag cttttcaagt ggtggatgac atcctcgaca tcaccgccac ccaggaagag     720
ttgggtaaaa ccgctggtaa agatgtcaaa gcccaaaaag ccaccatcc cagtctcctc     780 ggtttggaag cttcccgggc ccaggcccaa agtttgattg accaggccat tgtcgccctg     840
gaaccctttg ccctccgc cgagccctc caggcgatcg ccgaatatat tgttgccaga     900
aaatattga                                                            909
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 9
gtnggngcrg gcacncaycc                                                  20
```

```
<210> SEQ ID NO 10
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 10
tcgcgrgcra trttsgtsar rtg                                              23
```